United States Patent [19]
Langenaeken et al.

[11] Patent Number: 5,345,632
[45] Date of Patent: Sep. 13, 1994

[54] UNDERFRAME FOR MEDICAL EXAMINATION TABLE

[75] Inventors: Rene Langenaeken, Saint Georges sur Meuse; Claude Martin, Trooz, both of Belgium

[73] Assignee: General Electric CGR S.A., Issy les Moulineaux, France

[21] Appl. No.: 869,963

[22] Filed: Apr. 17, 1992

[30] Foreign Application Priority Data

Apr. 18, 1991 [FR] France ................... 91 04815

[51] Int. Cl.⁵ .............. A61G 7/005; A61G 7/012; A61G 13/04; A61G 13/06
[52] U.S. Cl. ............................. 5/601; 5/610; 108/4; 108/7
[58] Field of Search ................... 5/601, 610, 611; 378/209; 108/4, 7, 8

[56] References Cited

U.S. PATENT DOCUMENTS

| 2,680,046 | 6/1954 | Stava | 5/601 |
| 4,603,845 | 8/1986 | Schmedemann | 5/610 |
| 5,149,074 | 9/1992 | Jarin | 5/601 |

FOREIGN PATENT DOCUMENTS

| 1357371 | 2/1964 | France . | |
| 2542604 | 9/1984 | France | 5/601 |
| 893770 | 4/1962 | United Kingdom | 5/601 |

Primary Examiner—Alexander Grosz
Attorney, Agent, or Firm—Nilles & Nilles

[57] ABSTRACT

A medical examination table comprises a pedestal to which an end of a rocker is hinged. An underframe is fixed rotationally to the other end of the rocker. By acting on the two axes of rotation, the table may enable motions that are as different as a simple raising motion and tilting motions of various amplitudes in one direction or another. The advantage of the invention is that it provides a simplification of the industrial-scale manufacturing of tables with or without a rocker.

20 Claims, 6 Drawing Sheets

FIG_1

FIG_2

FIG_3-a

FIG_3-b

FIG_4

FIG_5

FIG_6

UNDERFRAME FOR MEDICAL EXAMINATION TABLE

BACKGROUND OF THE INVENTION

1. Field of the Invention

The invention relates to a medical examination table that can be used essentially in the field of radiology. It is possible, however, to conceive of its use in other fields of medicine, for example in nuclear medicine or in the field of ultrasonics. The particular feature of radiological medical tables is that they can be used to orient the patient in space in various ways while at the same time also providing for various functions such as those relating to myelography, tomography, cardiography, angiography, etc.

2. Description of the Prior Art

A medical examination table normally comprises a pedestal laid on or fixed to the ground and an underframe holding a patient-bearing plate. The underframe can be shifted in relation to the pedestal, and the patient-bearing plate can be moved translationally in relation to the underframe. The movements of the underframe may enable, firstly, elevation so that it can receive patients in the low position when they lie on the patient-bearing plate and then raise them so that these patients are presented in a more ergonomic way to the practitioner who is supposed to work on them during the radiological examination.

Furthermore, the underframe should also be capable of tilting, notably in myelography. While the patient is strapped to the plate, the underframe should be capable of taking vertical positions with the patient's feet below and his head up, or a reverse vertical position, also called a Trendelenbourg position, in which the patient's head is pointed downwards. The motions of the patient-bearing plate in relation to the underframe are normally motions of longitudinal and lateral translation, so that certain parts of the patient's body are presented to irradiation by X-rays when the picture is taken or the radiological study is made.

Traditionally, there are two known classes of tables given the diversity of the functions to be carried out. A first class relates to the tables that can be used in tomography, as well as in general radiology. These tables essentially comprise, from the viewpoint of the invention, the function of elevation as well as, accessorily to the present problem, a possibility of angular orientation of the X-ray beam in relation to the patient. This angular orientation corresponds to the needs manifested in tomography. In practice, with the tables of this class, the patient always reclines horizontally on the patient-bearing plate. He does not, for example, ever have to be strapped to it.

The other class of tables relates to tables that can be used inter alia for the myelographic function. Essentially, their underframe tilts in both directions. In practice, for this type of tilting table, there are three philosophies. In one case, before the underframe is made to tilt in one direction or in the other, it is raised in such a way that the ends of the underframe do not strike the ground at the instant of tilting. In the second case, the tilting motion is coupled to a motion of longitudinal shift of the underframe, so as to prevent the same problem. Naturally, in both cases, there are electronic safety circuits designed to prevent any positive action that would result in such a collision. In the first and second cases, the tilting is symmetrical: +90°/−90°.

In the third case, the tilting of the underframe is dissymmetrical, i.e. 90° vertically and 15° to 20° in the Trendelenbourg position, but it is achieved by a single mechanism. The myelographic examination is ruled out in this use but this type of underframe covers the majority of applications at a favorable cost of equipment. There is no elevation for this type of table.

The problem to be resolved by the manufacturer of such tables is that of low-cost series production. It is known, for example, that for the manufacture of these tables, the factories may be laid out as follows. Assembling stations fitted out with specialized equipment are ideally located in the factory. As and when they are completed, the tables are gradually brought closer to each of these work stations. If three type of tables are manufactured, it is necessary to plan for a threefold organization in terms of work stations and specialized equipment. This is cumbersome to manage and is also costly, and the specialized machines are themselves costly. It is therefore seen to be necessary to make tables of a single type which, depending on the equipment with which they are provided, are capable of fulfilling one function or another or even several functions.

Indeed, in applications of standard radiology and tomography, the underframe is normally borne by a vertical, motor-driven type of lift mechanism, the patient-bearing plate being motor-driven in lateral and longitudinal translation on the underframe. By contrast, for applications where the tilting is required, the underframe is fixedly joined to a circle sector element with a shape substantially identical to that of a semicircle. The rim of this circle sector element is provided with a rack with which there is engaged a toothed wheel fixed to the end of a motor shaft. When the motor runs, the circle sector rotates on itself in moving past the shaft. It then drives the tilting of the underframe vertically in one direction or another. This approach using a circle sector, which may be replaced by systems using synchronous belts or chains, is incompatible with the making of a lift mechanism, except at the cost of bulky and very complex machinery. The result thereof is that the classes of tables are completely different from one another.

A table of a tilting type that can be used for examinations in the non-horizontal position, as in patent No. GB-A-2 026 206. Similarly, other examples of such tables can be seen in the French patent applications Nos. 2 224 963 and 2 542 604. In every case, it is seen that the addition of a lift mechanism to the sector would lead to a very complicated mechanical approach.

SUMMARY OF THE INVENTION

An object of the invention is the overcoming of the above-mentioned drawbacks, notably the resolving of the problems of industrial-scale manufacture by proposing a table structure that can be suited, in a simple way, to the manufacture of a table of one class or the other or even a table enabling uses in both classes. The principle of the invention consists in the use, in the mechanism joining the pedestal to the underframe, of an intermediate part hereinafter called a rocker. This rocker is movable with respect to the pedestal, and the underframe is movable with respect to the rocker. In practice, the underframe has no direct links with the pedestal except by means of the rocker. To simplify the explanation, it may be said that if only one motor is used, it is possible to obtain a use according to the third mode of operation described above. If, on the contrary, the table is fitted out with two motors, it will naturally be capable of working according to the first or second modes of operation but also according to the third one.

An object of the invention, therefore, is to provide a medical examination table comprising a pedestal and an underframe to bear a patient-bearing plate, said table comprising an intermediate rocker that mechanically connects the pedestal to the underframe, two axes of rotation and driving means to prompt, with rotations about these axes, the shifting of the rocker with respect to the pedestal and of the underframe with respect to the rocker.

BRIEF DESCRIPTION OF THE DRAWINGS

The invention will be understood more clearly from the following description and from the accompanying drawings. These drawings are given purely by way of an indication and in no way restrict the scope of the invention. Of these figures.

DETAILED DESCRIPTION OF THE PREFERRED EMBODIMENTS

Figure 1:
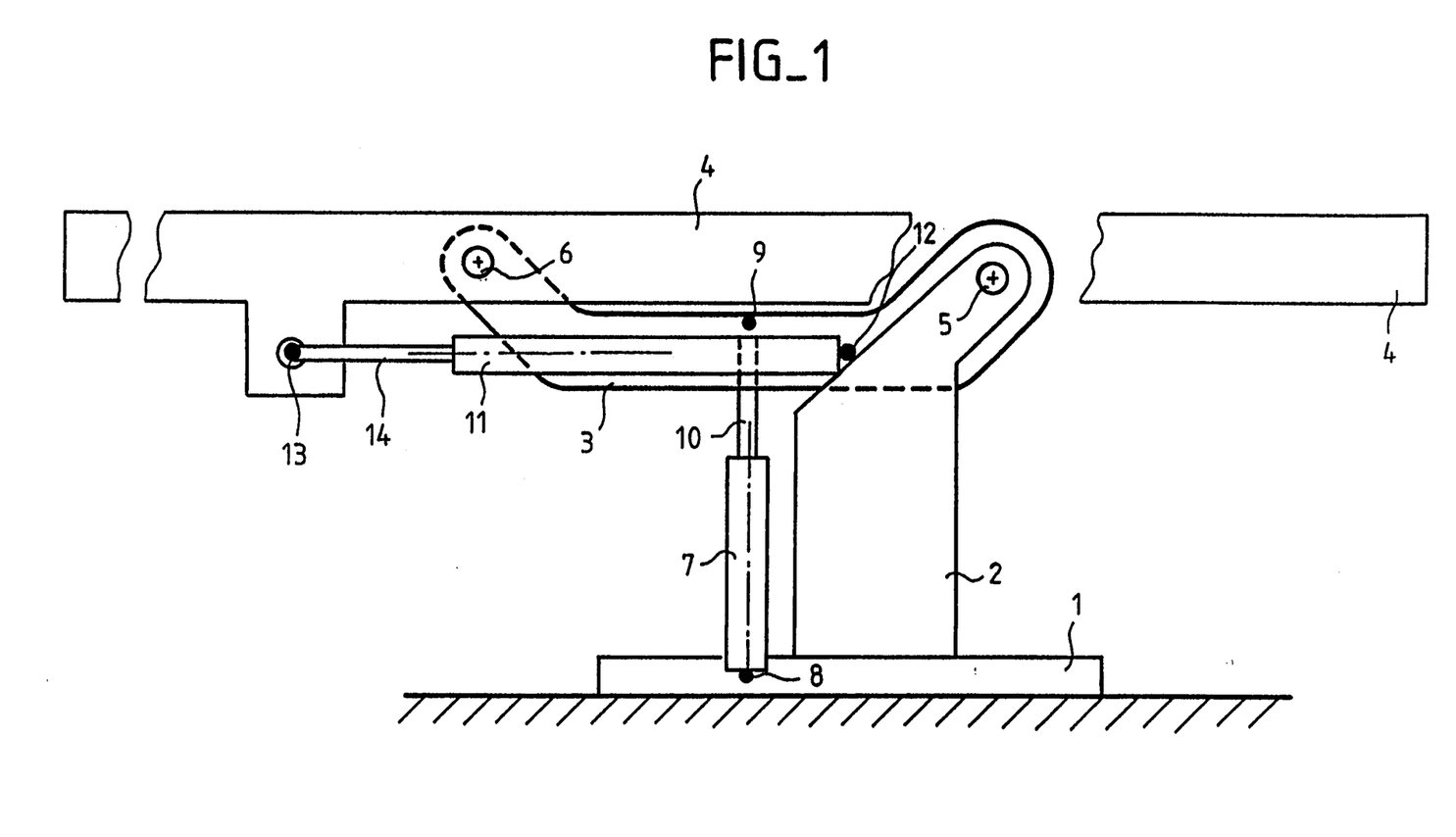
FIG. 1 shows a front view of an examination table constructed according to the invention.

FIG. 1 shows a medical examination table constructed according to the invention. This table has a pedestal formed by a base 1 resting on the ground and a column 2 extending upwardly from the base 1. For various reasons of asymmetry of tilt, the pedestal may be offset to the right or to the left of the table. A rocker 3 is mounted rotationally on the column 2. An underframe 4 of the table is mounted rotationally on the rocker 3. The column 2 is connected to the rocker 3 by means of a shaft 5 enabling rotation of the rocker 3 with respect to the column 2. The rocker 3 is linked to the underframe 4 by means of a shaft 6 which enables the rotation of the underframe 4 with respect to the rocker. The patient-bearing plate, though not shown, is normally placed above the underframe 4.

To drive these rotations, according to the invention, one or two motors are available. In a preferred embodiment, the motors comprise actuators or jacks, preferably double-action differential hydraulic or mechanical actuators or jacks, with non-return valves (for safety) if they are hydraulic. The actuators are only schematically illustrated in the drawings. A first actuator 7 is supported on the pedestal 1 by a pivot 8 and on the rocker 3 by a pivot 9. For a given position of extension of the rod 10 of the jack 7, the rocker 3 has a given orientation with respect to the column 2. The rotation of the underframe 4 about the rocker 3 is driven by an actuator 11 fixed by a first pivot 12 to the rocker and fixed by a second pivot to an end 13 of the underframe 14. Here again, for a given extension of the rod 14 of the jack or actuator 11, the underframe 4 takes a given orientation with respect to the rocker 3. The pivots 8, 9, 12 and 13 preferably comprise small pins, the rotational axes of which are, like the rotational axes of the shafts 5 and 6, perpendicular to the plane of FIG. 1.

The different cut-aways and dashed lines of FIG. 1 make it possible to understand that the underframe 4 is held solely by the pivot 13 and by the shaft 6 and that the rocker is held solely by the shaft 5 and the pivot 9. Consequently, it is deduced therefrom that the ends of the underframe 4 jut out with respect to its fastening to the shafts 6 and 13.

Figure 2:
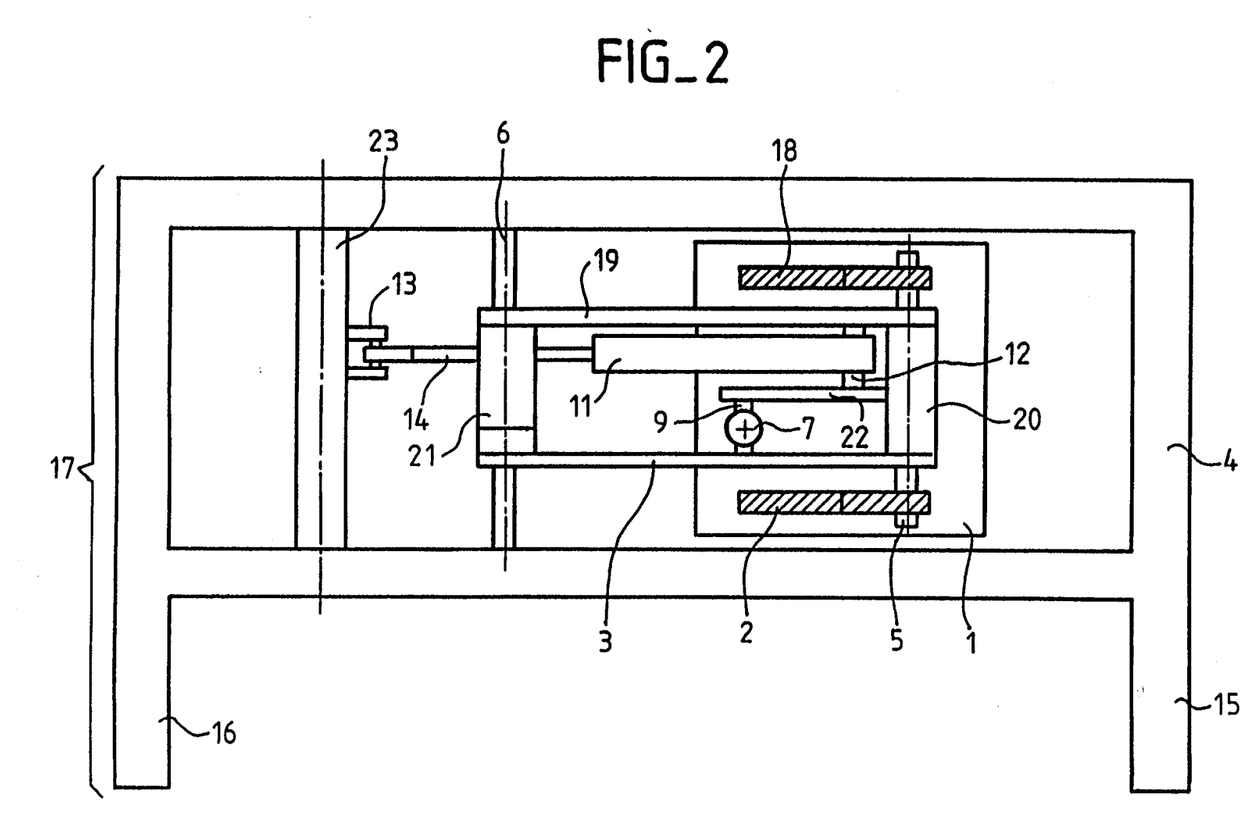
FIG. 2 shows a top view of the table of FIG. 1.

Referring to FIG. 2, underframe 4 has a rectangular frame provided with two projecting flanges 15 and 16 located on the lower side of the drawings. In practice, the practitioner assumes a position on the side where these flanges 15 and 16 are located, and his feet thus do not butt against the base 1. Normally, the top of the column 2 is not designed to go completely through the underframe 4, so that the patient-bearing plate and/or the other elements constituting the table may be laid on the entire surface of the underframe 4. Furthermore, the patient-bearing plate does not occupy this entire surface but has a width smaller than the width 17 of this underframe and thus may be shifted therein laterally in a standard way.

FIG. 2 shows that the column 2 is actually constituted chiefly by two flat, parallel columns 2 and 18 forming a bracket and constituting the chief parts of the base. In a preferred embodiment, the columns 2 and 18 are fixed by machine welding to the base 1. At their tops, columns 2 and 18 hold the shaft 5 by bearings. The illustrated rocker 3 is itself also provided with two flat metal bars 3 and 19 respectively. As shown in FIG. 1, each of these bars may be substantially trough-shaped. At the top of the edges of these bars 3, 19, there are mounted bearings in which the shafts 5 and 6 are engaged. The bars 3 and 19 of the rocker are fixed to each other by machine welding, with hollow spacers 20 and 21 being provided on either side of their ends.

A flat rest 22 is also fixed by welding to the spacer 20 through which the shaft 5 passes. Rest 22 enables the fastening of the two pivots 9 and 12. The pin of the pivot 9 is fixed between the bracket 22 and the arm 19 of the rocker. The actuators 7 and 11 are respectively hinged on each of these pivots with bearings at their ends. At its end to the left in the drawing, the underframe 4 comprises a spacer 23 to which there is fixed the pin of the pivot 13. The end of the actuator 11 is hinged to the pin of pivot 13. In one example, the length of the underframe 4 is in the range of 900 mm, and the length of the rocker between the shafts 5 and 6 is in the range of 835 mm.

Figure 3A:
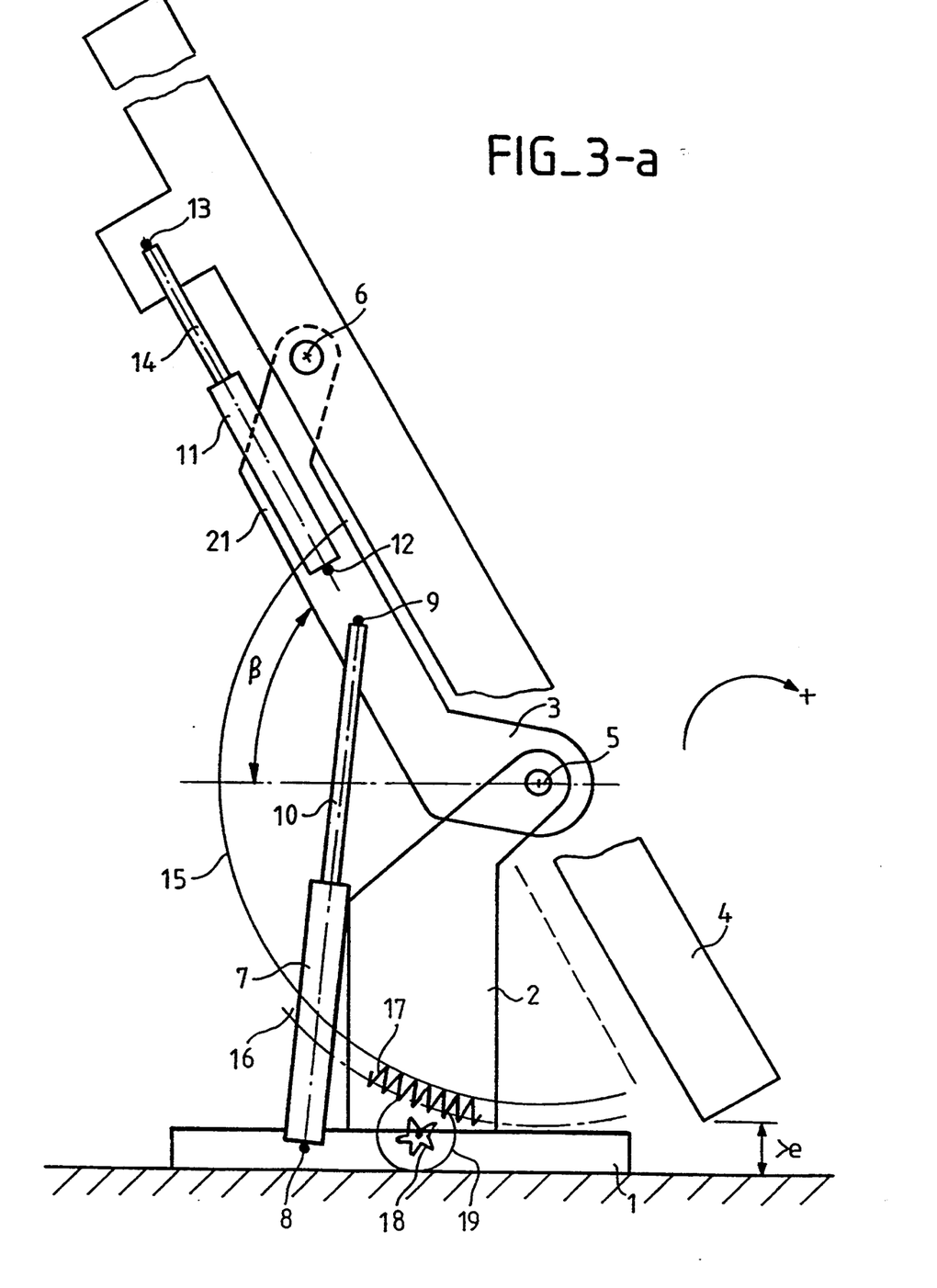
FIGS. 3a and 3b and FIG. 4 show front views of inclining positions of the table of FIG. 2.
Figure 3B:
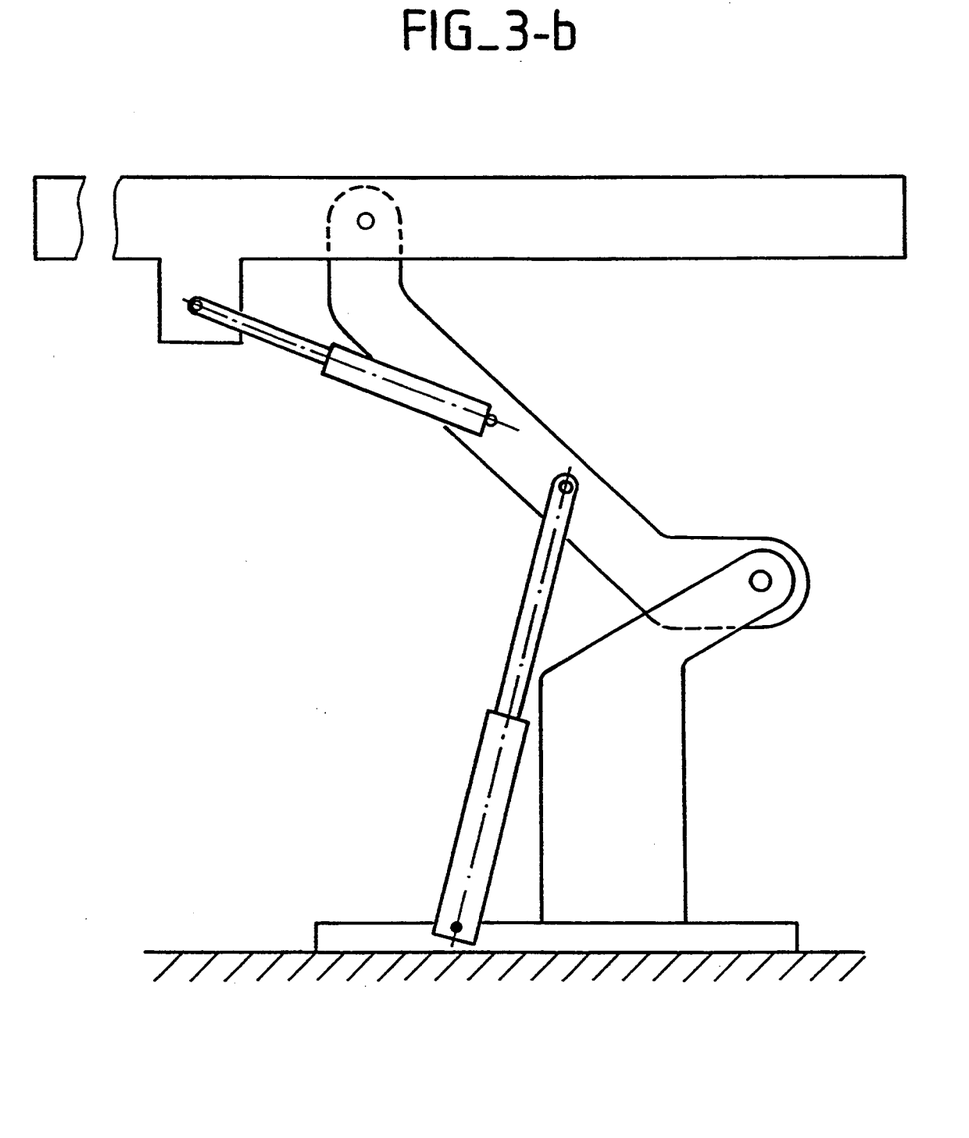
Figure 4:
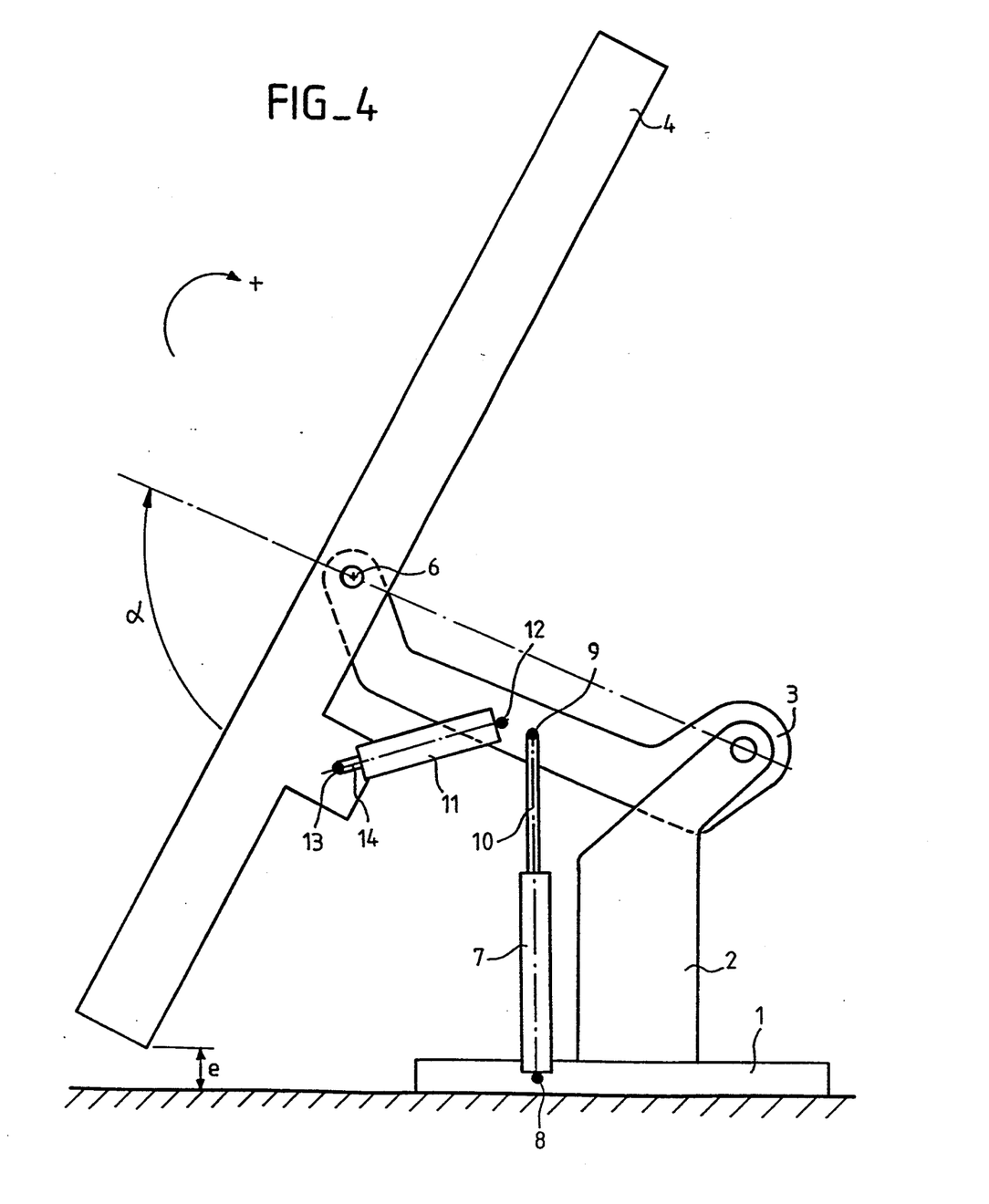

FIGS. 3a, 3b and 4 show the various positions taken by the table of the invention when either or both of the actuators 7 and 11 is or are in the extended position. FIG. 3a shows the angle of inclination $\beta$ taken by the rocker 3 with respect to the horizontal, or rather with respect to the base 1. As for FIG. 4, it shows the orientation $\alpha$ taken by the underframe 4 in relation to the rocker 3.

The fastening pivots 12 and 9 have been shifted, in FIGS. 3 and 4, in relation to the positions that they occupied in FIGS. 1 and 2, firstly to simplify the explanation and, secondly, to show that these pivots may have other positions on the rocker than the preferred positions indicated in FIGS. 1 and 2. In the representations of FIGS. 3 and 4, the kinematics of the motions are modified by the position of the pivots. However, the principles of the invention remain unchanged. The position of the pivots can thus be adapted to a desired mode of kinematic behavior. Thus, the actuators could have reverse operations for example: an actuator acting in a thrusting mode to prompt a defined tilt may, by a different choice of the position of its pivots, act in traction mode to prompt the same tilt. Similarly, instead of being both hinged on the rocker 3, the actuators 1, 11 may be both hinged on the pedestal 2 or on the underframe 4. In these cases, the actuators 7, 11 are respectively fixed by their shafts to the pedestal 2 and the rocker 3 and to the pedestal 2 and the underframe 4, or else to the pedestal 2 and the underframe 4 and to the rocker 3 and to the underframe 4.

In FIG. 3a, assuming that the patient has placed his feet on the right-hand side of the underframe 4, he is raised to the vertical position solely by action of the extension of the actuator 7 and, moreover, by keeping the actuator 11 in its initial position. By contrast (FIG. 4), in the so-called Trendelenbourg position, the rod 14 of the actuator 11 is retracted so that the patient's head is at the bottom.

It is seen in FIG. 4 that, in a preferred way, when the rod 14 of the actuator 11 is retracted, the rod 10 of actuator 7 has been made, beforehand, to extend slightly from the actuator 7. This makes it possible to obtain a safety distance e that prevents the underframe 4 from butting against the ground and also to keep the tilting of the table below a minimum room ceiling height. This furthermore has another advantage: the mechanism described enables raising motions. For, in a preferred way, the height of the column 2 and the position of the underframe 4, as shown in FIG. 1, are designed in such a way that patient-bearing plate is quite close to the ground. Under these conditions, the patient can easily sit on the plate and stretch out on it. In practice, this position causes the patient-bearing plate to be at a height of less than 70 cm above the ground. By contrast, either for use in the Trendelenbourg position or quite simply to facilitate action by the practitioner, it is preferred to raise the underframe by a combined action of extension of the rod 10 of the actuator 7 and of withdrawal of the rod 14 of the actuator 11. It can be imagined for example (FIG. 3b) that if the rod 14 is made to withdraw into the body of the actuator 11, then the underframe 4 will be parallel to the ground at a substantial height. Thus, a "great height" has been defined for the apparatus, wherein the patient-bearing plate has been placed, in practice, at about 125 cm above the ground.

The table of the invention makes it possible to efficiently resolve the problems of industrial-scale manufacture referred to here above. Indeed, the same table structure will be chosen to manufacture tables that are capable of only raising motions or of only tilting motions, or to manufacture tables capable of raising motions or of tilting motions irrespectively of the amplitude of the motions. Indeed, to manufacture tables that can be used with a raising motion only, hence without the possibility of tilting, the action of the motors will be coupled. In practice, this is achieved by coupling the actuators 7 and 11 such that the angle $\alpha$ is always equal to the angle $\beta$. This equality is therefore a linear relationship. It is also possible, simply and by mechanical means, to obtain rotations that are related to one rotations that are related to one another by a linear relationship. For example, it is enough to replace the actuator 7 by a rotating motor which drives the rotation of the rocker about the pedestal (by a chain if necessary). By employing a gear system with a multiplier coefficient equal to 1, it is enough to prompt an identical rotation of the underframe about the rocker. Another chain may be required for this construction. In this case, there is only one motor and the table is raised or lowered by action of this motor in one direction or another.

The result thereof is that, for a table capable of raising motions, the complexity of the mechanism is low because only the shaft 6 is required. By contrast, it is easy to change to use in a tilting mode by providing the table with a second motor that is independent or partially coupled to the first motor, and by enabling the tilting motions referred to in FIGS. 3a, 3b and 4. It will be noted that this technique enables the modification of the tables at the premises of the customer himself, inasmuch as the customer has initially purchased a simple table and subsequently wishes to improve his equipment.

As a preferred motor-driving mode, actuators have been described herein. However the method of the invention is equally well applicable to machines provided with sectors and rotating motors. A sector 15 such as this is shown in FIG. 3a. This sector 15 is a circle sector which may or may not be centered on the axis of the shaft 5. A virtual center of rotation would enable a greater radius of gyration. At its periphery 16, sector 15 is provided with a rack 17 that engages with a gear wheel 18 of a rotating motor 19. In this case, the rocker 3 therefore has the shape of a sector provided at one diametrical end 21 with an extension to which there is fixed a bearing to make the shaft 6 rotate. In this case, the pivot 12 of the actuator 11 is fixed to the sector 15. Kinematic behavior of the same nature as described above is obtained.

BY contrast with the approaches used in the prior art, the invention therefore presents a second rotational shaft, the shaft 6, which enables the underframe 4 to be made to rotate with respect to the intermediate rocker 3 or 15. Naturally, other embodiments can be used. For instance, one or both of the actuators 7, 11 could be replaced with actuators connecting the pedestal 2 to the underframe 4, so long as the resulting arrangement permits pivoting of the rocker 3 and the underframe 4 with respect to the pedestal 2. What is essential is the presence, in the device of the invention, of two centers of rotation such as the shafts 5 and 6.

Figure 5:
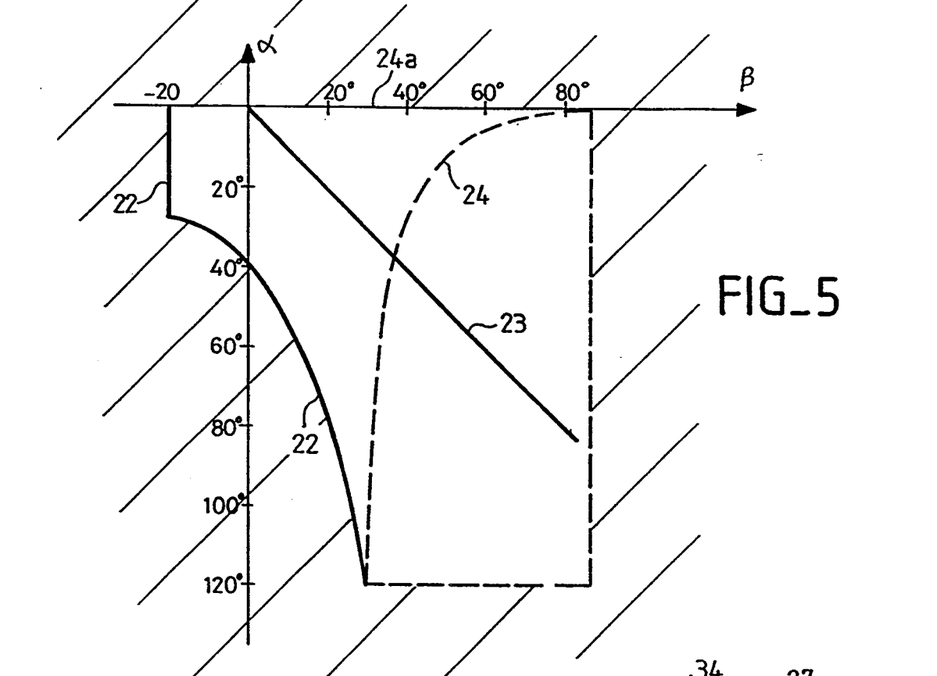
FIG. 5 shows a schematic drawing of the domain of the space available with the table of the invention.

FIG. 5 shows the usable domain of the orientation of the underframe 4 with respect to the rocker 3 and of the rocker 3 with respect to the pedestal 2. The angles are measured with their positive value in the trigonometrical sense. In the example shown, the angle $\beta$ may be slightly negative and the angle $\alpha$ always remains negative. The curve 22 shows the limit of the forbidden domain of the angle $\alpha$ for given values of the angle $\beta$. This curve may be loaded into a memory indicating the relationship between $\alpha$ and $\beta$. The curve 23 shows the operation of raising the table such that $\beta = \alpha$. The curve 24 shows a possible kinematic behavior that will be used to go from an angle $\beta = 90°$ (with $\alpha = 0$) to an angle $\alpha \approx 120°$ (with an angle $\beta \approx 30°$, which leads to a reverse vertical orientation: $120° - 30° = 90°$). The curve 24a shows the operation of tilting towards the vertical. The hatched parts of the graph show the unusable positions.

Figure 6:
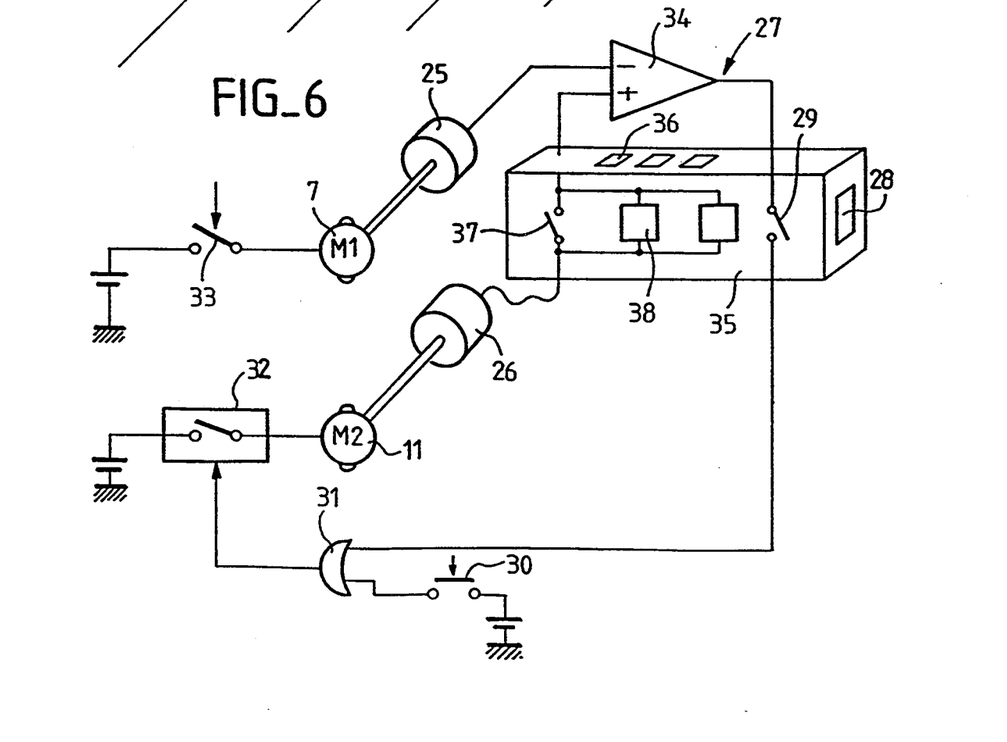
FIG. 6 shows a device for the automatic control of the different motors of the table to carry out a particular shift.

FIG. 6 will now be used to show how it is possible, schematically, to make the different motors work. This figure shows the motors 7 and 11 in a symbolic form M1 and M2. The shaft of each of these motors is connected, respectively, to a synchrodetector 25 and 26. These synchrodetectors are, for example, mounted on the shafts 5 and 6, respectively. These synchrodetectors deliver electrical signals that can be used in a control and regulation circuit 27. This control and regulation circuit 27 comprises a controller 28 that allows the motors to be independent.

In practice, when a switch 29 linked to controller 28 is open, actuation of the motor M2 is linked solely to action of a switch 30 which, through an OR logic gate 31, acts on a relay 32. The motor M1 is put into operation by positive action of a switch 33.

By contrast, when the movement of the motors has to be coupled, for example to bring about a raising motion (curve 33) or a tilting motion (curve 24), the switch 29 is closed. In this case, the signals of the synchrodetectors 25 and 26 are sent to a comparator 34. One of the signals, the one coming from the motor M2, is transmitted by means of a regulation circuit 35. This regulation circuit 35 has several modes of operation. Each of these modes is put into operation by action of control buttons of controller 28 such as buttons 36.

Should the raising motion be prompted, one of these buttons 36 has the function of (schematically) closing a switch 37 which enables direct comparison, in the comparator 34, of the signals emitted by the synchrodetectors 25 and 26. The comparator 34 therefore delivers an error signal which is then transmitted by means of a gate 31 to the relay 32. This has the effect of making the motor M2 rotate in a direction so as to keep the angles $\beta$ and $\alpha$ equal.

On the contrary, to meet the conditions of a curve 24 of tilt from $-90°$ to $+90°$, memories such as 38 will be used. These memories receive, at address inputs, the measurement of the angle $\alpha$ carried out by the synchrodetector 26 and delivery, at outputs, a value of the angle $\beta$ corresponding to them on the curve 24. A digitization of these functions is implemented in using analog/digital converters at inputs of the memories and digital/analog converters at outputs. The comparator 34 then compares the measurement of the real angle $\beta$ with the one that the angle $\beta$ should have if the equipment were to be on the curve 24. The comparator 34 then delivers an error signal capable of acting on the motor M2 so that the conditions of passing through this curve are met. Given that there may be several possible modes of reaching operations (change from raising mode to tilting mode, or else change from tilting mode to the low position so that the patient can get off the table) it may be necessary to provide for several memorized tables such as 38, each put into operation by means of button such as 36.

What is claimed is:

1. A medical examination table comprising:
   A. a pedestal;
   B. an underframe for supporting a patient bearing plate;
   C. a rocker having first and second opposed end portions pivotally connected to said underframe and to said pedestal, respectively;
   D. a first double acting actuator for pivoting said rocker with respect to said pedestal; and
   E. a second double acting actuator for pivoting said underframe with respect to said rocker.

2. A table according to claim 1, further comprising means for coordinating operation of said first and second actuators so as to effect designated movement of said underframe with respect to said pedestal.

3. A table according to claim 2, wherein said means for coordinating coordinates operation of said first and second actuators so as to effect raising of said underframe while maintaining said underframe horizontal.

4. A table according to claim 1, wherein said first actuator is connected to said pedestal and to said rocker, and said second actuator is connected to said rocker and to said underframe.

5. A table according to claim 1, wherein said actuators are hydraulic actuators.

6. A table according to claim 1, wherein at least one of said actuators comprises a mechanical actuator.

7. A table according to claim 6, wherein said mechanical actuator comprises a rack and a motor driven gear wheel coupled to said rack.

8. A table according to claim 1, wherein said underframe includes means for supporting said patient bearing plate such that said patient bearing plate overhangs said rocker to provide standing room for a practitioner standing by said table.

9. A table according to claim 8, wherein said means for supporting includes a rectangular frame and a plurality of flanges projecting from said frame.

10. A medical examination table comprising:
    A. a pedestal;
    B. an underframe for supporting a patient bearing plate;
    C. a rocker having first and second opposed end portions pivotally connected to said underframe and to said pedestal, respectively;
    D. a first double acting actuator for pivoting said rocker with respect to said pedestal, said first actuator being connected to said pedestal and to one of said rocker and said underframe; and
    E. a second double acting actuator for pivoting said underframe with respect to said rocker, said second actuator being fixed to said underframe and to one of said pedestal and said rocker.

11. A table according to claim 10, wherein said first actuator is connected to said pedestal and to said rocker, and said second actuator is connected to said rocker and to said underframe.

12. A table according to claim 10, wherein said actuators are hydraulic actuators.

13. A table according to claim 10, wherein at least one of said actuators comprises a mechanical actuator.

14. A table according to claim 13, wherein said mechanical actuator comprises a rack and a motor driven gear wheel coupled to said rack.

15. A table according to claim 10, wherein said underframe includes means for supporting said patient bearing plate such that said patient bearing plate overhangs said rocker to provide standing room for a practitioner standing by said table.

16. A table according to claim 15, wherein said means for supporting includes a rectangular frame and a plurality of flanges projecting from said frame.

17. A method of positioning a patient bearing surface of a medical examination table, said table including a pedestal, a rocker supported on said pedestal, and an underframe which is supported on said rocker and on which is supported said patient bearing table, said method comprising
    A. driving a first double acting actuator to pivot said rocker about said pedestal; and
    B. driving a second double acting actuator to pivot said underframe about said rocker.

18. A method according to claim 17, further comprising coordinating operation of said first and second actuators so as to effect designated movement of said underframe with respect to said pedestal.

19. A table according to claim 18, wherein said coordinating step comprises coordinating operation of said first and second actuators so as to effect raising of said underframe while maintaining said underframe horizontal.

20. A table according to claim 18, wherein said coordinating step comprises coordinating operation of said first and second actuators so as to effect raising of said underframe while tilting said underframe.

* * * * *